(12) United States Patent
Matsumoto et al.

(10) Patent No.: US 9,957,496 B2
(45) Date of Patent: May 1, 2018

(54) METHOD FOR REGULATING ACID RESISTANCE OF MICROBES

(71) Applicant: KABUSHIKI KAISHA YAKULT HONSHA, Minato-ku (JP)

(72) Inventors: Hoshitaka Matsumoto, Suginami-ku (JP); Mika Miura, Kawasaki (JP); Mayumi Kiwaki, Kokubunji (JP); Tohru Iino, Kawasaki (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 0 days. days.

(21) Appl. No.: 15/039,948

(22) PCT Filed: Dec. 3, 2014

(86) PCT No.: PCT/JP2014/081987
§ 371 (c)(1),
(2) Date: May 27, 2016

(87) PCT Pub. No.: WO2015/083743
PCT Pub. Date: Jun. 11, 2015

(65) Prior Publication Data
US 2017/0022491 A1    Jan. 26, 2017

(30) Foreign Application Priority Data

Dec. 4, 2013  (JP) .................. 2013-251362

(51) Int. Cl.
| | | |
|---|---|---|
| C12Q 1/68 | (2006.01) |
| C12N 9/00 | (2006.01) |
| A61K 35/74 | (2015.01) |
| C12Q 1/02 | (2006.01) |
| A23C 9/12 | (2006.01) |
| A23L 29/00 | (2016.01) |
| A23L 33/135 | (2016.01) |
| C12N 15/74 | (2006.01) |

(52) U.S. Cl.
CPC .............. *C12N 9/93* (2013.01); *A23C 9/12* (2013.01); *A23L 29/065* (2016.08); *A23L 33/135* (2016.08); *A61K 35/74* (2013.01); *C12N 15/746* (2013.01); *C12Q 1/02* (2013.01); *C12Q 1/689* (2013.01); *C12Y 602/01003* (2013.01); *A23V 2002/00* (2013.01); *C12Q 2600/156* (2013.01); *C12Q 2600/158* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2009/0170185 A1 | 7/2009 | Hayakawa et al. |
| 2010/0105955 A1 | 4/2010 | Alibhai et al. |
| 2010/0105963 A1 | 4/2010 | Hu |
| 2012/0201797 A1 | 8/2012 | Toi et al. |
| 2012/0329059 A1 | 12/2012 | Sako et al. |
| 2013/0004463 A1 | 1/2013 | Sugimoto et al. |
| 2013/0115665 A1 | 5/2013 | Hu et al. |
| 2014/0013658 A1* | 1/2014 | Silverman ............... C10G 3/00 44/308 |
| 2014/0377752 A1* | 12/2014 | Lee ....................... C12N 15/63 435/6.11 |

FOREIGN PATENT DOCUMENTS

| | | |
|---|---|---|
| JP | 2003-219861 A | 8/2003 |
| JP | 2007-175016 A | 7/2007 |
| JP | 2009-155221 A | 7/2009 |
| JP | 2012-504963 A | 3/2012 |
| JP | 2012-506715 A | 3/2012 |
| WO | 2007/029773 A | 3/2007 |
| WO | 2011/049154 A | 4/2011 |
| WO | 2011/083738 A | 7/2011 |
| WO | 2011/105335 A | 9/2011 |
| WO | 2013/105807 A | 7/2013 |

OTHER PUBLICATIONS

International Search Report dated Mar. 10, 2015 for PCT/JP2014/081987 filed on Dec. 3, 2014.

* cited by examiner

*Primary Examiner* — James S Ketter
(74) *Attorney, Agent, or Firm* — Oblon, McClelland, Maier & Neustadt, L.L.P.

(57) ABSTRACT

Provided are a method for regulating acid resistance of a microorganism by suppressing the expression of the fadD gene therein and a screening method for a microorganism having acid resistance by using the expression level of the fadD gene as an index. A method for regulating acid resistance of a microorganism, including suppressing the expression of fadD gene present in the microorganism.

20 Claims, 3 Drawing Sheets

Fig. 1

```
YIT 4008   -300  AGGCGGAACA ATCGGGGCAA AAGACCCGCA TTTTTCGTCT TCGCATCCCT GCTGCGTCAA
YIT 4065   -300  AGGCGGAACA ATCGGGGCAA AAGACCCGCA TTTTTCGTCT TCGCATCCCT GCTGCGTCAA
YIT 12272  -300  AGGCGGAACA ATCGGGGCAA AAGACCCGCA TTTTTCGTCT TCGCATCCCT GCTGCGTCAA

YIT 4008   -240  CTCGATTGGA TGACATCTAG GCAGTAGTCG AACGATCTCC AACCACTATC GGCAGTCTGT
YIT 4065   -240  CTCGATTGGA TGACATCTAG GCAGTAGTCG AACGATCTCC AACCACTATC GGCAGTCTGT
YIT 12272  -240  CTCGATTGGA TGACATCTAG GCAGTAGTCG AACGATCTCC AACCACTATC GGCAGTCTGT

YIT 4008   -180  TACCCAACAA TCAGAGCGCC AGTGTCCATC CACCACATAG AACCTCCCAA AACCTACGGT
YIT 4065   -180  TACCCAACAA TCAGAGCGCC AGTGTCCATC CACCACATAG AACCTCCCAA AACCTACGGT
YIT 12272  -180  TACCCAACAA TCAGAGCGCC AGTGTCCATC CACCACATAG AACCTCCCAA AACCTACGGT

YIT 4008   -120  TGCGTAGGCT TTTCCTACGG TTGCGTAAGG TGACGAGTTC GATGTGAACG ATTACAATCT
YIT 4065   -120  TGCGTAGGCT TTTCCTACGG TTGCGTAAGG TGACGAGTTC GATGTGAACG ATTACAATCT
YIT 12272  -120  TGCGTAGGCT TTTCCTACGG TTGCGTAAGG TGACGAGTTC GATGTGAACG ATCACAATCT

YIT 4008   -60   AAGGTTTGAG AGCGTTCGGC TTATGCTCGA ACGGCACTGA AAGGTTTACA GGAGCAAGAG
YIT 4065   -60   AAGGTTTGAG AGCGTTCGGC TTATGCTCGA ACGGCACTGA AAGGTTTACA GGAGCAAGAG
YIT 12272  -60   AAGGTTTGAG AGCGTTCGGC TTATGCTCGA ACGGCACTGA AAGGTTTACA GGAGCAAGAG
```

METHOD FOR REGULATING ACID RESISTANCE OF MICROBES

FIELD OF THE INVENTION

The present invention relates to a method for regulating acid resistance of a microorganism and a screening method for a microorganism having acid resistance.

BACKGROUND OF THE INVENTION

In recent years, among microorganisms, useful microorganisms which reach the intestinal tract in a viable state and exhibit effective health effects on the host have attracted attention. These useful microorganisms include certain bacteria of the genus *Lactobacillus* or the genus *Bifidobacterium*. Hitherto, there have been reported a number of health effects of bacteria of the genus *Lactobacillus* that include, in addition to the regulation of intestinal functions such as the improvement of constipation or diarrhea, an action to reduce the risk of breast cancer development (Patent Literature 1) and an interleukin-12 production-inducing ability (Patent Literature 2), and a number of health effects of bacteria of the genus *Bifidobacterium* that include a cholesterol absorption inhibitory action (Patent Literature 3) and an elastase activity inhibitory action (Patent Literature 4).

These useful microorganisms are required to reach the inside of the digestive tract in a viable state in order to effectively act in the digestive tract and to exert the health effects. However, there are a variety of growth inhibitory environments or growth inhibitors such as the temperature, the pH, oxygen, the osmotic pressure, and an acid until the useful microorganisms reach the inside of the digestive tract. Hence, it is important whether or not these microorganisms are resistant to the growth inhibitory environments or growth inhibitors upon utilizing these microorganisms. In particular, an acid is a major factor to determine whether or not these bacteria can reach the digestive tract. Hence, it can be said that acid resistance is one of the advantageous properties for useful microorganisms.

Among the useful microorganisms, in particular, bacteria of the genus *Bifidobacterium* are obligate anaerobes and vulnerable to oxygen, low pH and high acidity and have a number of difficulties in handling such as the proliferation at the time of manufacture or the survivability at the time of storage in a fermented food or beverage. In order to obtain the health effects of bacteria of the genus *Bifidobacterium*, it is considered that as many bacteria as possible are needed to reach the intestine in a viable state, and in particular, it is an important factor to increase the survivability of the bacteria in a food or beverage, namely, the arrival rate thereof to the intestine after eating or drinking. Hence, it can be said that bacteria of the genus *Bifidobacterium* having enhanced acid resistance and an increased arrival rate to the intestine are greatly required.

As useful microorganisms having acid resistance, *Lactobacillus casei* YIT9029 of the genus *Lactobacillus* (Patent Literature 5), *Bifidobacterium breve* YIT12272 of the genus *Bifidobacterium* (Patent Literature 6) and the like are known. These useful microorganisms having acid resistance are available as a number of commercial products in the form of various kinds of fermented milk products or viable pharmaceutical preparations. In particular, a fermented milk food or beverage has excellent palatability, and thus is easily taken or drunk continuously and suitable for administration of these useful microorganisms.

On the other hand, it is also required to weaken acid resistance of microorganisms in some cases, and thus it is significantly important to regulate acid resistance of a microorganism in a desired manner.

As an acid resistance regulating mechanism of microorganisms, pumping of protons to the outside of the bacterial cell by the ATP-dependent proton pump is mentioned. However, the ATP-dependent mechanism is presumed not to function as intracellular ATP of the microorganisms is depleted when the microorganisms are stored at a low temperature, and thus it is desirable to regulate acid resistance of microorganisms by utilizing an acid resistance regulating mechanism which functions even in a low temperature state as well.

The fadD gene is a gene that is confirmed to be present in some microorganisms and assumed to encode a long-chain-fatty-acid CoA ligase, an enzyme to convert a fatty acid to acyl-CoA.

However, the relationship between the fadD gene and acid resistance has not been known so far.

CITATION LIST

Patent Literature

Patent Literature 1: WO-A-2011/049154
Patent Literature 2: JP-A-2009-155221
Patent Literature 3: WO-A-2007/029773
Patent Literature 4: WO 2011/083738
Patent Literature 5: JP-A-2003-219861
Patent Literature 6: WO 2011/105335

SUMMARY OF THE INVENTION

Problems to be Solved by the Invention

The present invention relates to provide a method for regulating acid resistance of a microorganism by controlling the expression of the fadD gene therein and a screening method for a microorganism having acid resistance by using the expression level of the fadD gene as an index.

Means for Solving the Problems

The present inventors have comprehensively analyzed the genes of a particular strain of *Bifidobacterium breve* having acid resistance and its lineages among bacteria of the genus *Bifidobacterium* that are obligate anaerobes and usually do not have acid resistance, and have found that the transcription level of the fadD gene is significantly suppressed in a strain which exhibits acid resistance, acid resistance of microorganisms can be regulated by controlling the expression of the fadD gene, and the microorganisms having acid resistance can be selected through screening by using the expression level of the fadD gene or the like as an index.

Specifically, the present invention relates to following 1) to 16).

1) A method for regulating acid resistance of a microorganism, comprising controlling the expression of fadD gene present in the microorganism.

2) The method for regulating acid resistance according to 1), wherein the acid resistance is acid resistance which maintains a function in a low temperature state.

3) The method for regulating acid resistance according to 1) or 2), wherein the acid resistance is enhanced by inhibiting or suppressing the expression of fadD gene.

4) The method for regulating acid resistance according to 3), wherein a relative transcription level is 1% or less.

5) The method for regulating acid resistance according to 3) or 4), wherein a relative transcription level is 0.1% or less.

6) The method for regulating acid resistance according to 1) to 5), wherein the microorganism is a bacterium of the genus *Bifidobacterium*.

7) The method for regulating acid resistance according to 1) to 6), wherein the microorganism is *Bifidobacterium breve*.

8) A modified microorganism, wherein acid resistance is regulated by the method according to 1) to 7).

9) The modified microorganism according to 8), which has a property that a survival rate of the modified microorganism is 5 or more times higher than a survival rate of a microorganism before being modified when the modified microorganism that has been cultured to $1 \times 10^8$ cells/mL or more and then stored at a low temperature is treated with gastric acid at 37° C. for 60 minutes.

10) The modified microbe according to 9), which has a property that a survival rate of the modified microorganism is 10 or more times higher than a survival rate of a microorganism before being modified when the modified microorganism that has been cultured to $1 \times 10^8$ cells/mL or more and then stored at a low temperature is treated with gastric acid at 37° C. for 60 minutes and further treated with bile acid at 37° C. for 60 minutes.

11) The modified microorganism according to 8) to 10), wherein a sequence of a promoter which controls the transcription of fadD gene is modified.

12) The modified microorganism according to 8) to 11), wherein, in a promoter which controls the transcription of fadD gene, a base sequence 68 bp upstream of a start codon base is mutated from thymine (T) to cytosine (C).

13) A food or beverage, comprising the modified microorganism according to 8) to 12).

14) A pharmaceutical product, comprising the modified microorganism according to 8) to 12).

15) A screening method for selecting a microorganism having acid resistance, the method comprising measuring the presence or absence and/or expression level of fadD gene and/or an expression product thereof.

16). A microorganism having acid resistance, which is obtained by the method according to 15).

Effects of Invention

According to the present invention, it is possible to easily produce a modified microorganism having enhanced acid resistance without acquiring a mutant strain having acid resistance by the breed improvement. Acid resistance obtained herein is acquired by regulating the expression of the fadD gene and different from acid resistance that depends on ATP after culturing of the microorganisms, and thus the function is exerted even in a low temperature state. In addition, the modified microorganism exhibits improved survivability in vivo and thus can more reliably exert the health effects which microorganisms have. Furthermore, the modified microorganism exhibit improved survivability in low temperature storage, and thus it is possible to extend the storage period of the product. Furthermore, it is possible to culture the microorganism in a state having a higher acidity at the time of manufacturing the product, and thus it is possible to increase the number of microorganisms in the initial culture and to recover a great number of microorganisms by one time of culture.

In addition, according to the present invention, it is possible to easily produce a modified microorganism exhibiting weakened acid resistance. A great number of such modified microorganisms are killed by gastric acid, and thus they can be used as a microorganism which does not exert the health effects which microorganisms have in the stomach.

In addition, according to the screening method of the present invention, it is possible to simply select a microorganism having acid resistance through screening.

MODES FOR CARRYING OUT THE INVENTION

The nucleotide sequence (SEQ ID NO: 1) of the fadD gene in the present invention and a plurality of nucleotide sequences having high homology with this are registered in the NCBI database, and the fadD gene is assumed to encode a long-chain-fatty-acid CoA ligase which is an enzyme to convert a fatty acid to acyl-CoA.

In the present invention, to control the expression of the fadD gene includes to inhibit or suppress the expression of the fadD gene or to enhance or newly introduce the expression of the fadD gene. It is possible to enhance acid resistance by inhibiting or suppressing the expression of the fadD gene, and it is possible to weaken acid resistance by enhancing or newly introducing the expression of the fadD gene.

In the present invention, the target microorganism in which the expression of the fadD gene is controlled is not particularly limited. However, examples thereof may suitably include useful gram-positive bacteria, gram-negative bacteria, and yeasts which are required to be enhanced in acid resistance. Among them, gram-positive bacteria are preferable, and in particular, bacteria of the genus *Lactobacillus* and bacteria of the genus *Bifidobacterium* whose safety to the living body has been confirmed are preferable.

As the bacteria of the genus *Lactobacillus*, it is preferable to utilize bacteria belonging to the *Lactobacillus easel* group such as *Lactobacillus casei, Lactobacillus paracasei, Lactobacillus zeae*, and *Lactobacillus rhamnosus*, and it is possible to suitably utilize *Lactobacillus casei* and *Lactobacillus rhamnosus* in particular.

In addition, examples of the bacteria of the genus *Bifidobacterium* may include *Bifidobacterium breve, Bifidobacterium longum, Bifidobacterium infantis, Bifidobacterium adolescentis, Bifidobacterium bifidum, Bifidobacterium catenulatum, Bifidobacterium pseudocatenulatum*, and *Bifi-*

*dobacterium angulatum*, and it is possible to suitably utilize *Bifidobacterium breve* in particular.

Bacteria of the genus *Bifidobacterium* which exhibit useful physiological effects for human being are suitable as an application target of the present invention since they are obligate anaerobes and vulnerable to oxygen, low pH and high acidity and have a number of difficulties in handling such as the proliferation at the time of manufacture or the survivability at the time of storage.

In the present invention, to inhibit or suppress the expression of the fadD gene typically includes (i) to inhibit or suppress the transcription of the fadD gene into fadD mRNA and (ii) to inhibit or suppress the translation of fadD mRNA into fadD protein. However, it is not limited thereto.

For inhibition of expression of the fadD gene, the gene may be disrupted or deleted through the insertion-inactivation method in which a DNA fragment entirely different from a target gene is inserted into the gene, or the stepwise double crossover method in which the entirety or a portion of a target gene is deleted by stepwise homologous recombination. Particularly, the stepwise double crossover method is preferably employed.

Specifically, when the entirety or a portion of the fadD gene is deleted, two regions sandwiching the deletion region are separated from chromosomal DNA or separated following amplification by PCR, and the two DNA fragments are cloned into a plasmid vector (e.g., pYSSE3) which can replicate in *Escherichia coli* but cannot in a microorganism of interest, so that the fragments are aligned in the same direction as the original direction. Subsequently, the resultant recombinant plasmid DNA is introduced, through electroporation or a similar technique, into a microorganism in which deletion is caused to occur. Through PCR or a similar technique, there is selected, from the resultant antibiotic-resistant clones, a clone in which the plasmid has been inserted into the chromosome through recombination in a region homologous to the above-cloned region upstream or downstream of the target deletion region. The thus-obtained clone is repeatedly subcultured in a medium containing no antibiotic, to thereby select clones which have lost antibiotic resistance through removal of the plasmid from the chromosome by recombination between flanking homologous regions and through disappearance of the plasmid in bacterial growth. Through PCR or a similar technique, there can be selected, from the thus-obtained clones, a clone in which the fadD gene region has been deleted.

Suppression of expression of the fadD gene may be carried out through the so-called RNA interference method in which a short RNA fragment complementary to the 5'-end region of mRNA of the gene is synthesized, or a method in which a regulatory gene or a region for controlling expression of the gene is disrupted or deleted. Particularly, modification of a region for controlling expression of the gene is preferred. Specifically, the level of transcription of the fadD gene into mRNA can be increased or reduced by modifying the sequence of a promoter for controlling transcription of the fadD gene. As used herein, to reduce the transcription level of the fadD gene into mRNA refers to that the relative transcription level is reduced to 1% or less and preferably 0.1% or less. The relative transcription level refers to one that is obtained by dividing the expression level of the fadD gene in a microorganism having a modified type fadD gene by the expression level (for example, expression level of mRNA) of the fadD gene in a microorganism having a wild type fadD gene among the microorganisms of the same species. As used herein, the microorganism having a wild type fadD gene refers to a microorganism in which the base sequence of the fadD gene or its promoter is not mutated and the expression of the fadD gene is not enhanced or introduced or inhibited or suppressed, and the microorganism having a modified type fadD gene refers to a microorganism in which the expression of the fadD gene is enhanced or introduced or inhibited or suppressed through modification or the like of the base sequence of the fadD gene or its promoter.

In addition, as used herein, to modify the sequence of the promoter refers to a case in which a portion of the bases (for example, about from 1 to 20 bases, preferably from 1 to 10 bases, and more preferably from 1 to 5 bases) constituting the DNA fragment in the promoter region is substituted or deleted or a case in which from 1 to several bases (for example, from 1 to 10 bases and preferably 1 to 5 bases) are added or inserted. For example, in the promoter of fadD gene, it refers to that the base sequence 68 bp upstream of a start codon base is substituted from thymine (T) to cytosine (C).

Meanwhile, enhancement of expression of the fadD gene may be carried out through, for example, a method in which a recombinant plasmid carrying the gene is introduced into a microorganism of interest; a method in which the gene is integrated into another site of the chromosome through site-specific recombination, to thereby increase the number of copies of the gene in a microorganism; or a method in which the level of expression of the gene is increased by modifying a promoter region of the gene and increasing the transcription level of the gene into mRNA. Particularly preferred is a method of increasing the number of copies of the gene.

Introduction of the fadD gene into another microorganism may be carried out through, for example, the competence method using DNA uptake ability, the protoplast PEG method using a protoplast, or electroporation using high-voltage pulses. In addition, integration of the fadD gene into the chromosome of a microorganism may be carried out through homologous recombination or site-specific integration.

Further, as a specific method of increasing the number of copies of the fadD gene, there may be mentioned a method in which the fadD gene (including the original promoter sequence and ribosome-binding site of the gene) or the polynucleotide (prepared by ligating only a polypeptide-encoding region of the gene to the downstream of a promoter and a ribosome-binding site which have been separated from another gene or chemically synthesized) is cloned into a plasmid having a plurality copies per microbial cell, and the plasmid is introduced into microbial cells through electroporation or a similar technique. By using the method, the number of copies of the gene can be increased in microbial cells.

In the present invention, a modified microorganism which has been regulated so as to exhibit enhanced acid resistance by controlling the expression of the fadD gene can be employed for producing a food, beverage, or pharmaceutical product effectively exhibiting various physiological effects that are intrinsic to the microorganism, since acid resistance thereof has been enhanced. In addition, a modified microorganism which has been regulated so as to exhibit weakened acid resistance can be employed, for example, as a microorganism which exhibits various physiological effects that are intrinsic to the microorganism before reaching the stomach and does not act in the stomach.

As used herein, acid resistance means resistance to all acids which a microorganism of interest has, in particular, gastric acid or bile acid, and more specifically, it refers to acid resistance which functions even in a low temperature state. That is, the acid resistance is clearly different from ATP-dependent acid resistance that is presumed not to function in a low temperature state.

As used herein, the low temperature state means to be in a state of from 0 to 10° C. Specifically, storage in a low temperature state (low-temperature storage) is mentioned, and examples thereof include storage at 10° C. or lower for 7 days or longer, storage at 5° C. or lower for 14 days or longer, and storage at 4° C. or lower for 14 days or longer.

The enhancement of acid resistance means that acid resistance of the modified microorganism is enhanced as compared to the microorganism before being modified as the expression of the fadD gene is inhibited or suppressed by modifying the fadD gene or its promoter of the microorganism. More specifically, a property is mentioned that the survival rate (the proportion of the number of living bacteria after a gastric acid treatment with respect to the number of living bacteria before the gastric acid treatment) of the modified microorganism is 5 or more times and preferably 10 or more times higher as compared to the survival rate of the microorganism before being modified when the modified microorganism that has been cultured to $1 \times 10^8$ cells/mL or more is stored at a low temperature under the condition of 4° C. for 7 days and then treated with gastric acid at 37° C. for 60 minutes. Alternatively, a property is mentioned that the survival rate is 30 or more times and preferably 50 or more times higher when stored under the condition of 4° C. for 14 days or that the survival rate is 100 or more times and preferably 150 or more times higher when stored under the condition of 4° C. for 19 days. In addition, a property is mentioned that the survival rate (the proportion of the number of living bacteria after a gastric acid-bile acid continuous treatment with respect to the number of living bacteria before the gastric acid-bile acid continuous treatment) of the modified microorganism is 10 or more times and preferably 30 or more times higher as compared to the survival rate of the microorganism before being modified when the modified microorganism that has been cultured to $1 \times 10^8$ cells/mL or more is stored at a low temperature under the condition of 4° C. for 7 days, then treated with gastric acid at 37° C. for 60 minutes, and further treated with bile acid at 37° C. for 60 minutes, or a property is mentioned that the survival rate is 100 or more times and preferably 200 or more times higher when stored under the condition of 4° C. for 14 days. As used herein, as the gastric acid and bile acid, for example, there may be used artificial gastric juice (pH: 3.3) and artificial bile (1.0% bovine bile (Oxgall)) described in WO 2011/105335.

When the modified microorganism of the present invention is incorporated into a food or beverage or in a pharmaceutical product, living cells, heated cells (dead cells), or lyophilized cells of the microorganism may be employed. Alternatively, a cultured product containing the microorganism may be employed, or processed cells of the microorganism may be employed. Preferably, living cells of the microorganism are employed.

When the modified microorganism of the present invention is employed in a pharmaceutical product, the microorganism may be mixed with a solid or liquid pharmaceutical nontoxic carrier, and the mixture may be administered in the form of a conventional pharmaceutical product. Examples of such a pharmaceutical product include solid products such as tablet, granules, powder, and capsule; liquid products such as solution, suspension, and emulsion; and lyophilized products. Such a pharmaceutical product may be prepared through a customary technique for pharmaceutical production. Examples of the aforementioned pharmaceutical nontoxic carrier include glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, and saline. If necessary, the pharmaceutical product may appropriately contain a conventional additive such as a stabilizer, a humectant, an emulsifier, a binder, an isotonizing agent, or an excipient.

The modified microorganism of the present invention may also be incorporated into a food or beverage in addition to the aforementioned pharmaceutical product. When the microorganism is incorporated into a food or beverage, the microorganism may be employed as is, or mixed with various nutritional ingredients. The resultant food or beverage can be employed for producing a health food or food material effectively exhibiting various physiological effects that are intrinsic to the microorganism, since acid resistance has been regulated in a desired manner. Specifically, when the modified microorganism obtained through the method of the present invention is incorporated into a food or beverage, the microorganism may be appropriately mixed with an additive which can be used in a food or beverage, and the mixture may be prepared, through conventional means, into a form suitable for edible use; for example, granules, particles, tablet, capsule, or paste. The microorganism may be added to a variety of foods; for example, processed meat products (e.g., ham and sausage), processed fish products (e.g., kamaboko and chikuwa), bread, confectionary, butter, and powdered milk. Alternatively, the microorganism may be added to beverages such as water, fruit juice, milk, refreshing beverages, and tea beverages. As used herein, the food or beverage encompasses animal feeds.

Examples of the food or beverage of the present invention include fermented foods and beverages produced by use of the microorganism of the present invention, such as fermented milk, lactic acid bacteria beverages, fermented soybean milk, fermented fruit juice, and fermented plant extract. Such a fermented food or beverage may be produced through a customary method. For example, a fermented milk product may be produced through the following procedure. Firstly, only the modified microorganism of the present invention is inoculated into a sterilized milk medium, or the modified microorganism and another microorganism are simultaneously inoculated into the medium, followed by culturing, and the cultured product is homogenized to thereby yield a fermented milk base. Subsequently, a separately prepared syrup is added to and mixed with the fermented milk base, and the mixture is homogenized by means of, for example, a homogenizer, followed by addition of a flavor to the resultant mixture, to thereby yield a final product. The thus-produced fermented milk product may be in any form, such as a plain-type product containing no syrup (sweetener), a soft-type product, a fruit-flavor-type product, a solid product, or a liquid product.

The microorganism produced through the method of the present invention and regulated so as to exhibit enhanced acid resistance exhibits high acid resistance even in a low temperature state, and thus exhibits high survivability in a product containing acid. Therefore, a reduction in number of living cells or an increase in rate of cell death is suppressed during low-temperature storage of the product. In addition, the specification of the product is readily maintained, and the product effectively exhibits general physiological effects (e.g., regulation of intestinal functions) of a microorganism (e.g., a bacterium of the genus *Lactobacillus*). When acid resistance of a bacterial strain of the genus *Lactobacillus* or

*Bifidobacterium* which originally has a specific physiological effect (e.g., anticancer effect or *Helicobacter pylori* eradication effect) is enhanced through the method of the present invention, the bacterial strain can be applied to various foods and beverages, and the physiological effect of the bacterial strain can be enhanced by virtue of improvement of the survivability of the bacterial strain.

In addition, the microorganism produced through the method of the present invention and regulated so as to exhibit weakened acid resistance are mostly killed by gastric acid. Therefore, the microorganism can be utilized as a microorganism which exhibits various physiological effects that are intrinsic to the microorganism before reaching the stomach and does not act in the stomach.

As described above, acid resistance of microorganisms is enhanced when the expression of the fadD gene is inhibited or suppressed. Therefore, a microorganism exhibiting acid resistance can be selected through screening by using the expression level of the fadD gene and/or an expression product thereof as an index. That is, the microorganism exhibiting acid resistance can be selected through screening by measuring the presence or absence and/or expression level of the fadD gene and/or an expression product thereof. Examples of an expression product of a gene may include mRNA and a polypeptide, and examples of the polypeptide may include a polypeptide of an amino acid sequence represented by SEQ ID NO: 9.

For measurement of the expression level of the fadD gene and/or an expression product thereof, the presence or absence of the fadD gene in a microorganism, the number of copies of the gene, or the expression level thereof is determined through southern hybridization, northern hybridization, DNA microarray, or RT-PCR by use of a probe or primer which can detect the fadD gene or mRNA derived therefrom. Alternatively, the amount of a polypeptide is determined through ultraviolet absorption method, spectrophotometry such as BCA method (bicinchoninic acid method) or Lowry method, or the electrophoresis. A microorganism of interest (microorganism having acid resistance) is selected on the basis of the presence or absence of the fadD gene or an expression product thereof or the expression level thereof.

In order to effectively perform the aforementioned modification of the gene or screening of microorganisms, preferably, there is employed a recombinant vector containing the polynucleotide of SEQ ID NO:1 or a portion thereof, a primer for PCR or RT-PCR containing a portion (fragment) of the polynucleotide of SEQ ID NO:1, a primer for PCR or RT-PCR which can amplify the polynucleotide of SEQ ID NO:1 or a portion thereof, or a nucleic acid fragment for hybridization containing a polynucleotide which specifically hybridizes with the polynucleotide of SEQ ID NO:1 or a portion of the polynucleotide.

The nucleic acid fragment (e.g., primer) which may be employed in the present invention is generally, for example, a nucleotide chemically synthesized on the basis of information on the nucleotide sequence of the gene of the present invention. Preferably, such a nucleotide has a partial nucleotide sequence corresponding to the nucleotide sequence of SEQ ID NO: 1, and includes 10 to 50 consecutive nucleotides (preferably 15 to 35 consecutive nucleotides).

The present invention will next be described in more detail by way of Examples.

EXAMPLES

Example 1 Confirmation of Mutation Site in Promoter Region of the fadD Gene

Figure 1:
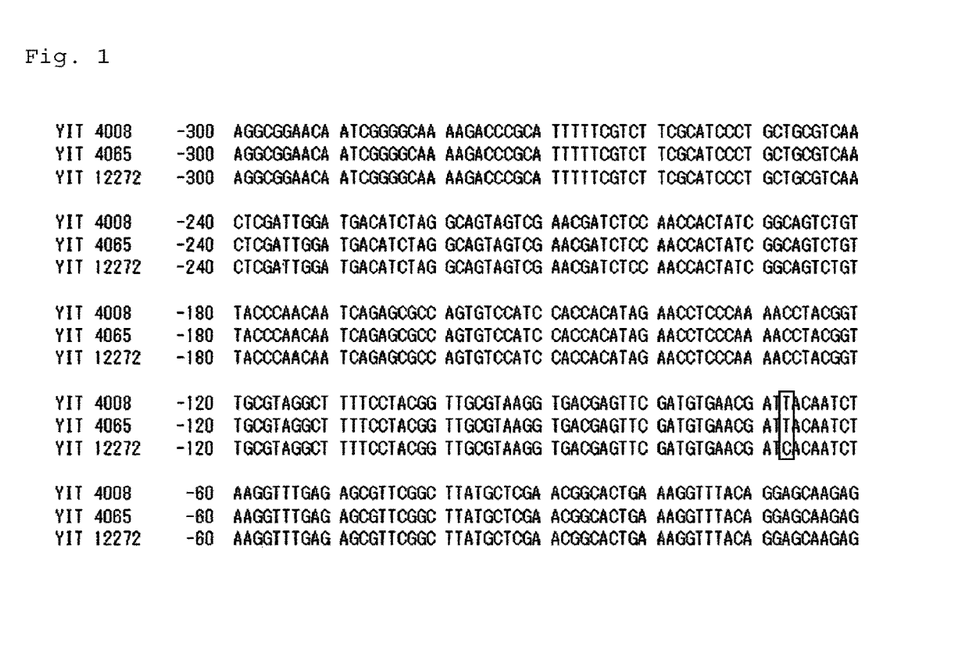
FIG. 1 is a diagram for comparing the base sequences in the region of a promoter which controls the transcription of the fadD gene in *Bifidobacterium* (positions 1-300 of SEQ ID NO:6). The number of base 1 bp upstream of the start codon base is denoted as −1. The portion surrounded by a square is the site at which mutation is present.

The base sequences in the vicinity of the fadD gene of *Bifidobacterium breve* YIT 12272 (FERM BP-11320) having acid resistance and *Bifidobacterium breve* YIT 4008 (FERM BP-4538) and *Bifidobacterium breve* YIT 4065 (FERM BP-6223) which were its lineages were determined by the dye terminator method in accordance with the conventional method and compared with one another. As a result, it has been considered that there is a possibility that the base sequence 68 bp upstream of the start codon base in the promoter of fadD gene in YIT 12272 has been mutated from thymine (T) to cytosine (C), resulting in a change in the transcription level of the fadD gene. The mutation site in the promoter of the fadD gene is illustrated in FIG. 1.

Example 2 Analysis of Transcription Level of the fadD Gene

*Bifidobacterium breve* YIT 12272 having acid resistance and *Bifidobacterium breve* YIT 4008 and *Bifidobacterium breve* YIT 4065 which were its lineages were anaerobically cultured at 37° C. using MILS medium (Iwata and Morishita, Letter in Applied Microbiology, vol 9, 165-168, 1989). For anaerobic culture, the gas phase was replaced with nitrogen gas, seal was made with a butyl stopper, followed by static culture.

Total RNA was extracted from each strain in the logarithmic growth phase using the RNeasy Mini Kit (manufactured by QIAGEN). Then, a cDNA solution was prepared using 1 μg of the RNA and the PrimeScript 1st strand cDNA Synthesis Kit (manufactured by TAKARA BIO INC.). Real-time PCR (95° C. for 30 seconds, followed by 40 cycles of 95° C. for 5 seconds and 60° C. for 34 seconds) was performed using the cDNA solution prepared from each strain as a template, the SYBR Premix Ex Taq (manufactured by TAKARA BIO INC.) and the primers shown in Table 1 with the ABI PRISM 7500 (manufactured by Applied Biosystems by Thermo Fisher Scientific Inc.), to thereby measure the transcription levels of the fadD gene and 16S rRNA gene. It should be noted that the correction between samples was performed using the transcription level of 16S rRNA gene as an internal standard.

TABLE 1

| Target | Forward | Reverse |
| --- | --- | --- |
| fadD | CACCTCCTATGACTGGGATCTGAC (SEQ ID NO: 2) | TGACGATATTGCGGATTTGTTC (SEQ ID NO: 3) |
| 16rRNA | ATCGGGCTTTGCTTGGTG (SEQ ID NO: 4) | GAGCATCCGGCATTACCAC (SEQ ID NO: 5) |

Figure 2:
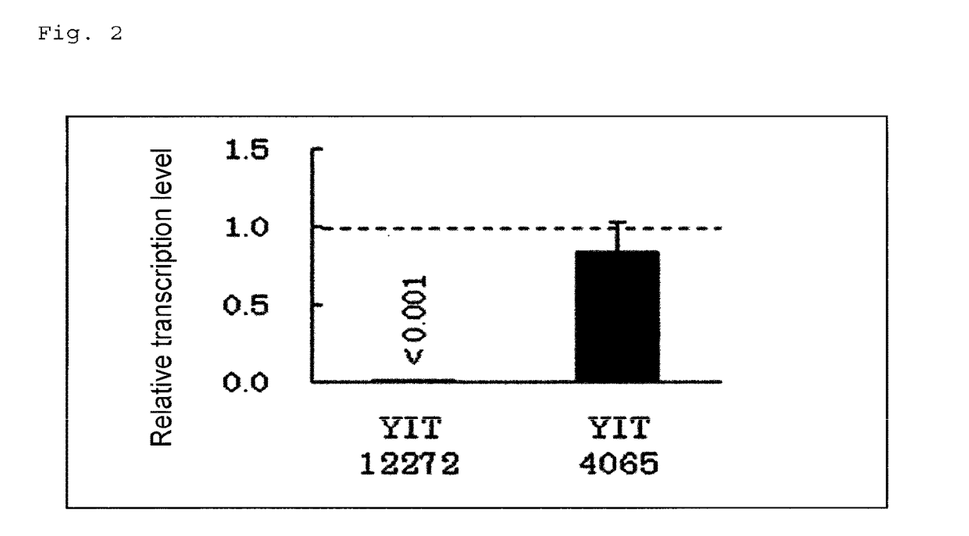
FIG. 2 is a graph illustrating the relative transcription levels of the fadD gene (with respect to YIT 4008 strain).

The transcription level of the fadD gene in each strain is illustrated in FIG. 2 as a relative value with respect to YIT 4008 having a wild type fadD gene. The transcription level of the fadD gene in YIT 4065 was comparable with that in YIT 4008. However, the transcription level greatly reduced in YIT 12272 in which mutation occurred upstream of the fadD gene, and the relative transcription level thereof was 0.1% or less as compared to that of YIT 4008 and it was 0.1% or less even when compared to that of YIT 4065.

Example 3 Production of Transformant Having Wild Type fadD Gene Introduced and Relative Transcription Level of the fadD Gene in Transformant In order to examine the influence of the fadD gene on acid resistance, a transformant HM0102 strain obtained by introducing the fadD gene promoter and the fadD gene derived from YIT 4008 into YIT 12272 was prepared.

First, PCR (30 cycles of 96° C. for 15 seconds, 60° C. for 30 seconds and 72° C. for 150 seconds) was performed using the genomic DNA of YIT 4008 as a template, the KOD-Plus—(TOYOBO CO., LTD.) and the primers shown in Table 2 with the iCycler (manufactured by Bio-Rad Laboratories, Inc.), to thereby amplify a DNA fragment (SEQ ID NO: 6) containing the full length fadD gene, 300 bp upstream thereof, and 100 bp downstream thereof.

TABLE 2

| Name | Sequence |
| --- | --- |
| fadD-u300-Eco-Fw | CG<u>GAATTC</u>AGGCGGAACAATCGGGGCAAA (SEQ ID NO: 7) |
| fadD-d100-Eco-Rv | CG<u>GAATTC</u>AAGCAACTAGAACGCCTCGGCT (SEQ ID NO: 8) |

The underlined portion indicates the recognition sequence of restriction enzyme.

Figure 3:
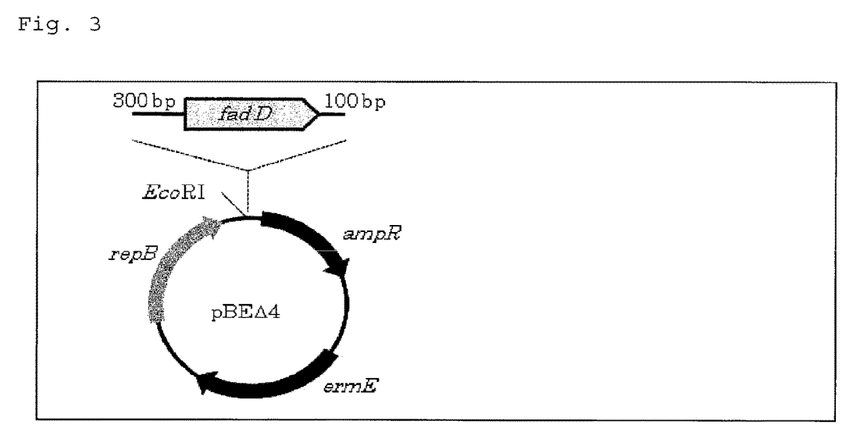
FIG. 3 is diagram for producing a plasmid DNA for fadD gene expression.

The amplified DNA fragment and the pBEL4 vector described in JP-A-H10-262670 were digested with restriction enzyme EcoRI in accordance with the conventional method described in the same literature. The resultant digested fragments were ligated using the DNA Ligation Kit Ver. 2.1 (manufactured by TAKARA BIO INC.), to thereby produce a plasmid DNA for fadD gene expression under the control of the original promoter. The preparation diagram of the plasmid DNA is illustrated in FIG. 3.

The plasmid DNA was introduced into *Bifidobacterium breve* YIT 12272 by the electroporation method. Electroporation was performed using the GENE PULSER II (manufactured by Bio-Rad Laboratories, Inc.) under the conditions of 200Ω, 25 µF, and 18 kV/cm. Thereafter, the electroporation reaction solution was smeared on the MILS agar medium supplemented with 3 µg/mL of erythromycin and anaerobically cultured at 37° C. for 72 hours using the AnaeroPack (manufactured by MITSUBISHI GAS CHEMICAL COMPANY, INC.). The colony thus produced was obtained as the transformant HM0102 strain, the plasmid DNA was extracted by the alkaline method in accordance with the conventional method, and it was confirmed that the introduced plasmid DNA was retained.

Meanwhile, as a control of the HM0102 strain, the HM0101 strain was produced by introducing the pBEΔ4 vector alone into YIT 12272 in a similar manner.

The expression level of the fadD gene was measured for the three strains of YIT 12272, the HM0101 strain, and the HM0102 strain by the method described in Example 2. It should be noted that the culture of the HM0101 strain and the HM0102 strain which were transformants was performed by using the Y-MILS medium obtained by adjusting the yeast extract concentration of MILS medium to 1.5% and adding erythromycin so as to have a final concentration of 3 µg/mL.

Figure 4:
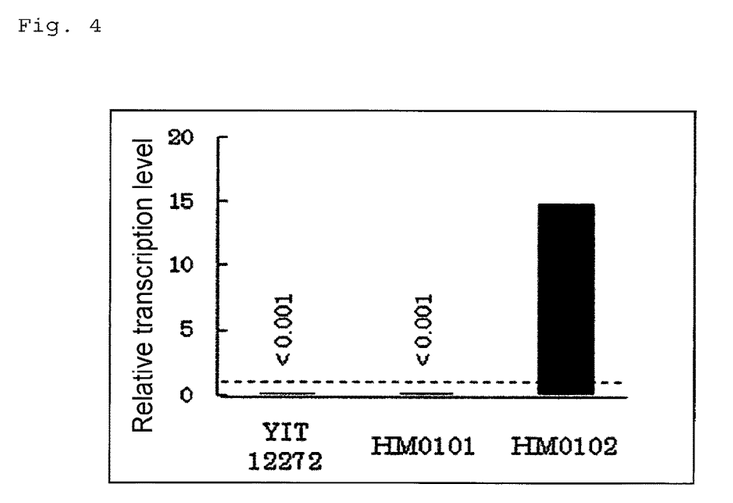
FIG. 4 is a graph illustrating the relative transcription levels of the fadD gene (with respect to YIT 4008 strain) of transformants.

As a result of the measurement of the transcription level of the fadD gene of each strain, it was found that the transcription level of the fadD gene is high in the HM0102 strain into which a wild type fadD gene promoter and the fadD gene have been introduced as compared to YIT 12272 and the HM0101 strain. The transcription level of the fadD gene in each strain is illustrated in FIG. 4 as a relative value with respect to the transcription level of the fadD gene in YIT 4008.

Example 4 Measurement of Acid Resistance of Transformant

The acid resistance after low-temperature storage was measured in order to more clearly confirm acid resistance of the transformant. Each culture solution of the HM0101 strain (number of bacteria after culture: $8.5 \times 10^8$ cells/mL) and the HM0102 strain (number of bacteria after culture: $8.8 \times 10^8$ cells/mL) which had been anaerobically cultured for one night to $1 \times 10^8$ cells/mL or more was anaerobically and statically stored at 4° C. in the medium described in Example 3 above. The culture solutions were subjected to the gastric acid-bile acid continuous treatment on days 0, 7, 14, 19 and 29 after the start of storage, and acid resistance of both strains was compared to each other.

The gastric acid-bile acid continuous treatment was performed as follows using artificial gastric juice and artificial bile described in Patent Literature 6. First, 0.5 mL of the culture solution which had been stored at 4° C. was added to 10 mL of the artificial gastric juice (pH3.3) which had been kept warm at 37° C. in advance, and the mixture was stirred to perform the gastric acid treatment at 37° C. for 60 minutes. Then, 1 mL of artificial bile (1.0% Oxgall) and 5 mL of a reaction buffer (buffer solution containing 0.5% sodium chloride, 0.1% potassium chloride, and 0.3% sodium hydrogen and having a pH of 8.0) were added to 2 mL of the solution after being subjected to the gastric acid treatment, and the mixture was stirred to continuously perform the bile acid treatment at 37° C. for 60 minutes. 1 mL of each of the treated solutions at 0 minutes and 60 minutes after the gastric acid treatment and 120 minutes after the gastric acid and bile acid continuous treatment was appropriately diluted, then smeared on the TOS propionic acid agar medium (manufactured by Yakult Pharmaceutical Industry Co., Ltd.), and anaerobically cultured using the AnaeroPack (manufactured by MITSUBISHI GAS CHEMICAL COMPANY, INC.) at 37° C. for 72 hours. The number of colonies formed was multiplied by the total dilution factor to determine the number of living bacteria per 1 mL of the culture solution, and the proportion of the number of living bacteria after each treatment with respect to the number of living bacteria at 0 minutes after the acid treatment was adopted as the survival rate.

Here, the HM0102 strain has a wild type fadD gene, the HM0101 strain has a mutant type fadD gene, and the genes other than the fadD gene are exactly the same in both strains, thus the HM0102 strain corresponds to a microorganism before being subjected to the fadD gene modification and the HM0101 strain corresponds to a fadD gene modified microorganism.

Figure 5:
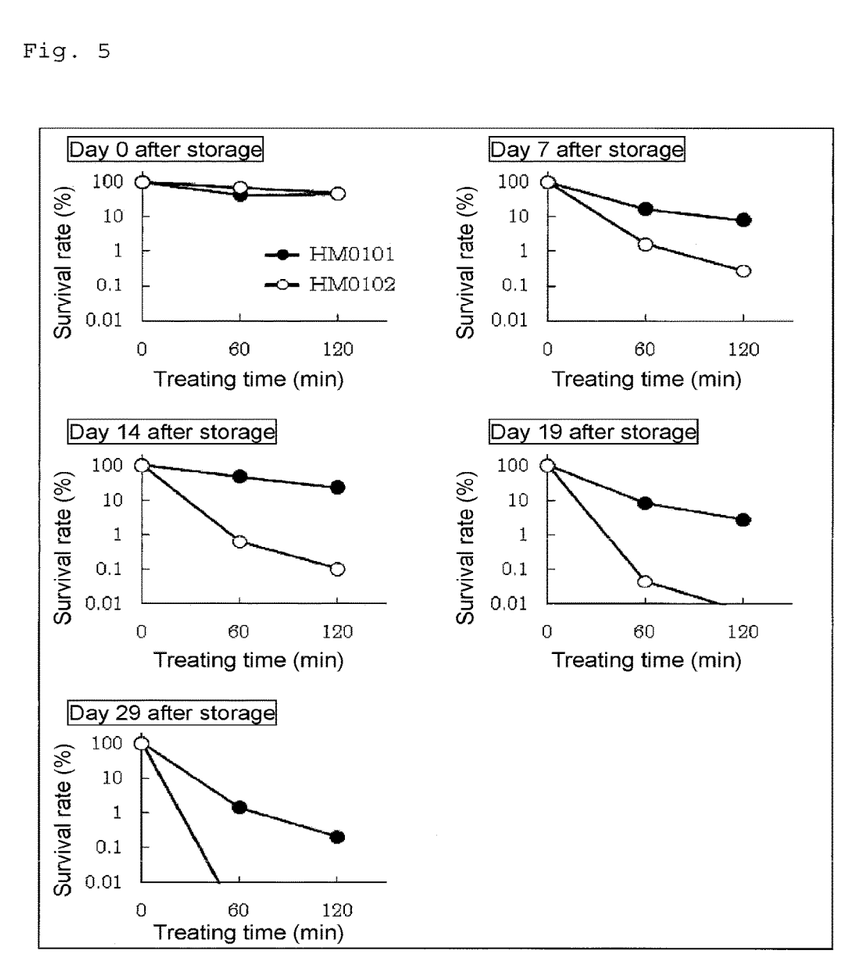
FIG. 5 is graphs illustrating the survival rate after the acid-bile acid continuous treatment.

The measurement results of the number of living bacteria and survival rate of both strains after the gastric acid treatment and after the gastric acid and bile acid continuous treatment are illustrated in FIG. 5, and the ratio of the survival rate of the HM0101 strain to that of the HM0102 strain is shown in Table 3. As a result, the survival rate after the gastric acid treatment and after the gastric acid and bile acid continuous treatment significantly reduced in the HM0102 strain into which a wild type fadD gene promoter had been introduced as the low-temperature storage days had passed. However, the width of a reduction in survival rate was small in the HM0101 strain and acid resistance thereof had been enhanced as compared to that of the HM0102 strain. It was also indicated by the ratio of the survival rate that acid resistance of the HM0101 strain had been enhanced. The enhancement of acid resistance was remarkably observed in the case of being placed in a low temperature state.

TABLE 3

| Number of storage days | Ratio of survival rate after gastric acid treatment | Ratio of survival rate after gastric acid and bile acid continuous treatment |
| --- | --- | --- |
| Day 7 | 10.5 | 30.7 |
| Day 14 | 76.8 | 232 |
| Day 19 | 187 | * |
| Day 29 | * | * |

Ratio of survival rate = survival rate of HM0101 strain/survival rate of HM0102 strain.
* It is not possible to calculate the ratio since the number of bacteria of the HM0102 strain is below the detection limit.

From the results above, it has been revealed that an increase in transcription of the fadD gene acts to reduce acid resistance of a microorganism, in particular, *Bifidobacterium breve*, on the contrary, inhibition or suppression of the transcription of the fadD gene acts to enhance acid resistance of a microorganism, in particular, *Bifidobacterium breve*. Hence, it is considered that to reduce the transcription level of the fadD gene can be utilized for the enhancement of acid resistance of a microorganism without depending on the intracellular ATP content after culture.

The invention claimed is:

1. A method for modifying acid resistance of a microorganism, the method comprising:
   modifying expression of fadD gene present in the microorganism; and
   selecting a microorganism having modified acid resistance.

2. The method according to claim 1, wherein the acid resistance is acid resistance maintained under a temperature of from 0 to 10° C.

3. The method according to claim 1, wherein the modifying of the expression of the fadD gene comprises inhibiting or suppressing the expression of the fadD gene such that the acid resistance of the microorganism is enhanced.

4. The method according to claim 3, wherein the modifying of the expression of the fadD gene comprises inhibiting or suppressing a relative transcription level of the fadD gene to 1% or less.

5. The method according to claim 3, wherein the modifying of the expression of the fadD gene comprises inhibiting or suppressing a relative transcription level of the fadD gene to 0.1% or less.

6. The method according to claim 1, wherein the microorganism is a bacterium of the genus *Bifidobacterium*.

7. The method according to claim 1, wherein the microorganism is *Bifidobacterium breve*.

8. A method for regulating acid resistance of a microorganism, the method comprising:
   controlling expression of fadD gene present in the microorganism by modifying a transcription promoter of the fadD gene.

9. A modified microorganism, produced by regulating acid resistance of a microorganism by the method according to claim 8.

10. The modified microorganism according to claim 9, wherein the modified microorganism has a survival rate of 5 or more times higher than a survival rate of the microorganism before being modified when the modified microorganism that has been cultured to $1\times10^8$ cells/mL or more and then stored at a temperature of from 0 to 10° C. is treated with gastric acid at 37° C. for 60 minutes.

11. The modified microorganism according to claim 9, wherein the modified microorganism has a survival rate of 10 or more times higher than a survival rate of the microorganism before being modified when the modified microorganism that has been cultured to $1\times10^8$ cells/mL or more and then stored at a temperature of from 0 to 10° C. is treated with gastric acid at 37° C. for 60 minutes and further treated with bile acid at 37° C. for 60 minutes.

12. The modified microorganism according to claim 9, wherein, in the transcription promoter of the fadD gene, thymine (T) located 68 bp upstream of a start codon base of the fadD gene is changed to cytosine (C).

13. A food or beverage, comprising:
   the modified microorganism according to claim 9.

14. A pharmaceutical product, comprising:
   the modified microorganism according to claim 9.

15. A screening method for a microorganism having acid resistance, the method comprising:
   detecting the presence of fadD gene, absence of fadD gene, presence of an expression product of fadD gene, absence of an expression product of fadD gene, or a combination thereof, or measuring expression level of fadD gene, expression level of an expression product of fadD gene, or a combination thereof, in a microorganism;
   selecting a microorganism exhibiting inhibited or suppressed transcription of the fadD gene; and
   culturing the selected microorganism in a culture medium.

16. The method according to claim 8, wherein controlling of the expression of the fadD gene comprises changing thymine (T) located 68 bp upstream of a start codon base of the fadD gene to cytosine (C).

17. The modified microorganism according to claim 9, which is a bacterium of the genus *Bifidobacterium*.

18. The modified microorganism according to claim 9, which is *Bifidobacterium breve*.

19. The method according to claim 1, wherein the modifying of the expression of the fadD gene comprises enhancing the expression of the fadD gene such that the acid resistance of the microorganism is weakened.

20. The method according to claim 1, further comprising:
   culturing the microorganism having modified expression of fadD gene to $1\times10^8$ cells/mL or more, storing the microorganism at a temperature of from 0 to 10° C., and then treating the microorganism with gastric acid at 37° C. for 60 minutes,
   wherein the selecting of the microorganism having modified acid resistance comprises, after the treating with gastric acid, selecting the microorganism having a survival rate of 5 or more times higher as compared to a survival rate of the microorganism before being modified.

* * * * *

SEQUENCE LISTING

<160> NUMBER OF SEQ ID NOS: 9

<210> SEQ ID NO 1
<211> LENGTH: 2034
<212> TYPE: DNA
<213> ORGANISM: Bifidobacterium breve

<400> SEQUENCE: 1

```
ttgtcggtta tcaattcctt tacgcagcac accatcaatc tgacccgcaa ggcactcagg      60
ttgggatccg acttcgttca cccggttcac gacgacactc cggacgagcc cgattatctg     120
tccaatgccg atgtgccgca ggaagccaac atcgaactgc cgcacagcga cgattgggat     180
gacggccatc tgaccgtcac cgacatcgac ccggaaaccg gactgctcac cacgtccact     240
gccggcaatc cgcctctgga cgacggcacg tccatctacg acctgtatgc ggatcgcgcc     300
aagcgcatgg gtgacgaacc gctgtatacc tacaagtccg acaacgaatg ggtgaccgtc     360
accgccaatg agttcctcgc cgaagtgcgt gccgtggcca agggcctgct gcactacggc     420
atcaagaagg gcgacggcgt ggcgttcatg tgccgcacct cctatgactg ggatctgacc     480
gatgcggcca tcatggcctg cggcggcgtg ctggccacca tctacgacac cgactcggcc     540
gaacaaatcc gcaatatcgt caacaattct gacgcgcgtc tgctcatcgt gcaggattcc     600
gccatgcgag agaaggcgga aggcgccgtg gaggaatgcc cctcactcga gcgcatccta     660
tgcatcgaga ccggcgctct tgatgagatc aaggcctatg gtgccggcat ctcggacgag     720
gaactggatg agcgcattga ttcggtcaag aaaaccgatc tgtgctccat tgtgtacacc     780
tctggttcca ccgccgcgcc gaagggcgtg gagatgaccc acgagcacta ctgccagacc     840
gcgctgaacc tgccggacta catgcccgag ctgctgcaca acaagaagaa caccatcctg     900
ctgttcctgc cgcaggccca ctcctttgcc cgcgccatca attacatcgt cgtggcctcg     960
aatatgcata tctacatcgc cgccggcatc aagacgctga ttagtgattt gcaggtggct    1020
aagccgtcca tcatgattgt ggtgccgcgt gtgctggaga aggtgtacaa cgccgcctcc    1080
cagaaggccg gccatggccc caaggcgtg gtgttcgcct ccgccgtggt ggctgcccag    1140
aactacatga aggaaatctc cgccaacggc aaggccagtg cattgacccg tgcccgccgc    1200
gcggccttcg atccgattgt ctactcctca ctgcgtgagg tgctgggtgg acgcatgaag    1260
tggattgtgg ccggcggcgc gccgcttgac cctgaactgc ttgcgttctt ccgcggcgca    1320
```

```
agcgtgcccg tctacgaggg ctatggtctg accgaaacca ccgcaccatg cgcgttcaac    1380
ccgctgggaa ccccgttcca cgccgggtcc gtgggcgtcg cgttcccogg cttctcgctg    1440 cgtattgccg aggacggcga gatccaggtc aagggtcgcg ccgtgttccc gcgttatcac    1500
aagaacgatg aggccaccga gctgtcgttc accgaagatg gctggtatgc caccggagat    1560
ttgggccgta tcgacaacga tggcttcctg tacattaccg gccgcaagaa ggatctcatc    1620
atcaccgcag gtggcaagaa tgtggcgccg ggtccgattg aagaggccat tcagcgttgc    1680
gagttcgtgt cccaggcact ggtgctgggc gacaagcgtc cgttcatctc cgcgctgatt    1740
acgctggacg aggagtcttt gcgtccttgg ctggccgcca agggattgga cgagaacatg    1800
tctctggagg acgcctctca gaacgccgcc gtacgcgctg aggtccagaa gtggatcgat    1860
caggccaacg aaggcgtttc ccgcgccgaa tccgtgcgta agttcatcat cctgcctgag    1920
gagttcacac aggagaacgg cctgatgacc gcctccatga aggtcatccg ccccaaggtc    1980
atcaagcgct actccaccct cctcaacacc cagatgtaca ccaagaagaa gtaa          2034

<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 2
cacctcctat gactgggatc tgac                                            24

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
tgacgatatt gcggatttgt tc                                              22

<210> SEQ ID NO 4
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 4 atcgggctttgcttggtg                                                    18

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
gagcatccgg cattaccac                                                  19

<210> SEQ ID NO 6
<211> LENGTH: 2434
<212> TYPE: DNA
<213> ORGANISM: Bifidobacterium breve

<400> SEQUENCE: 6
```

```
aggcggaaca atcggggcaa aagacccgca tttttcgtct tcgcatccct gctgcgtcaa      60
ctcgattgga tgacatctag gcagtagtcg aacgatctcc aaccactatc ggcagtctgt     120
tacccaacaa tcagagcgcc agtgtccatc caccacatag aacctcccaa aacctacggt     180
tgcgtaggct tttcctacgg ttgcgtaagg tgacgagttc gatgtgaacg attacaatct     240
aaggtttgag agcgttcggc ttatgctcga acggcactga aaggtttaca ggagcaagag     300
ttgtcggtta tcaattcctt tacgcagcac accatcaatc tgacccgcaa ggcactcagg     360
ttgggatccg acttcgttca cccggttcac gacgacactc cggacgagcc cgattatctg     420
tccaatgccg atgtgccgca ggaagccaac atcgaactgc cgcacagcga cgattgggat     480
gacggccatc tgaccgtcac cgacatcgac ccggaaaccg gactgctcac cacgtccact     540
gccggcaatc cgcctctgga cgacggcacg tccatctacg acctgtatgc ggatcgcgcc     600
aagcgcatgg gtgacgaacc gctgtatacc tacaagtccg acaacgaatg ggtgaccgtc     660
accgccaatg agttcctcgc cgaagtgcgt gccgtggcca agggcctgct gcactacggc     720
atcaagaagg gcgacggcgt ggcgttcatg tgccgcacct cctatgactg ggatctgacc     780
gatgcggcca tcatggcctg cggcggcgtg ctggccacca tctacgacac cgactcggcc     840
gaacaaatcc gcaatatcgt caacaattct gacgcgcgtc tgctcatcgt gcaggattcc     900
gccatgcgag agaaggcgga aggcgccgtg gaggaatgcc cctcactcga gcgcatccta     960
tgcatcgaga ccggcgctct tgatgagatc aaggcctatg gtgccggcat ctcggacgag    1020
gaactggatg agcgcattga ttcggtcaag aaaaccgatc tgtgctccat tgtgtacacc    1080
tctggttcca ccgccgcgcc gaagggcgtg gagatgaccc acgagcacta ctgccagacc    1140
gcgctgaacc tgccggacta catgcccgag ctgctgcaca acaagaagaa caccatcctg    1200
ctgttcctgc cgcaggccca ctcctttgcc cgcgccatca attacatcgt cgtggcctcg    1260
aatatgcata tctacatcgc cgccggcatc aagacgctga ttagtgattt gcaggtggct    1320
aagccgtcca tcatgattgt ggtgccgcgt gtgctggaga aggtgtacaa cgccgcctcc    1380
cagaaggccg gccatggccc caagggcgtg gtgttcgcct ccgccgtggt ggctgcccag    1440
aactacatga aggaaatctc cgccaacggc aaggccagtg cattgacccg tgcccgccgc    1500
gcggccttcg atccgattgt ctactcctca ctgcgtgagg tgctgggtgg acgcatgaag    1560
tggattgtgg ccggcggcgc gccgcttgac cctgaactgc ttgcgttctt ccgcggcgca    1620
agcgtgcccg tctacgaggg ctatggtctg accgaaacca ccgcaccatg cgcgttcaac    1680
ccgctgggaa cccgttcca cgccgggtcc gtgggcgtcg cgttcccgg cttctcgctg    1740 cgtattgccg aggacggcga gatccaggtc aagggtcgcg ccgtgttccc gcgttatcac    1800
aagaacgatg aggccaccga gctgtcgttc accgaagatg gctggtatgc caccggagat    1860
ttgggccgta tcgacaacga tggcttcctg tacattaccg gccgcaagaa ggatctcatc    1920
atcaccgcag gtggcaagaa tgtggcgccg ggtccgattg aagaggccat tcagcgttgc    1980
gagttcgtgt cccaggcact ggtgctgggc gacaagcgtc cgttcatctc cgcgctgatt    2040
acgctggacg aggagtcttt gcgtccttgg ctggccgcca agggattgga cgagaacatg    2100
tctctggagg acgcctctca gaacgccgcc gtacgcgctg aggtccagaa gtggatcgat    2160
caggccaacg aaggcgtttc cgcgccgaa tccgtgcgta agttcatcat cctgcctgag    2220
gagttcacac aggagaacgg cctgatgacc gcctccatga aggtcatccg ccccaaggtc    2280
atcaagcgct actccaccct cctcaacacc cagatgtaca ccaagaagaa gtaagcagag    2340
```

```
ctcgagtaca gcaaaaggga gattccaatg gaatctccct ttgttataac cggtcgaagg      2400
ccgattccta gaagccgagg cgttctagtt gctt                                 2434
```

<210> SEQ ID NO 7
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 7

```
cggaattcag gcggaacaat cggggcaaa                                         29
```

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 8

```
cggaattcaa gcaactagaa cgcctcggct                                        30
```

<210> SEQ ID NO 9
<211> LENGTH: 677
<212> TYPE: PRT
<213> ORGANISM: Bifidobacterium breve

<400> SEQUENCE: 9

```
Leu Ser Val Ile Asn Ser Phe Thr Gln His Thr Ile Asn Leu Thr Arg
1               5                   10                  15

Lys Ala Leu Arg Leu Gly Ser Asp Phe Val His Pro Val His Asp Asp
            20                  25                  30

Thr Pro Asp Glu Pro Asp Tyr Leu Ser Asn Ala Asp Val Pro Gln Glu
        35                  40                  45

Ala Asn Ile Glu Leu Pro His Ser Asp Asp Trp Asp Asp Gly His Leu
    50                  55                  60

Thr Val Thr Asp Ile Asp Pro Glu Thr Gly Leu Leu Thr Thr Ser Thr
65                  70                  75                  80

Ala Gly Asn Pro Pro Leu Asp Asp Gly Thr Ser Ile Tyr Asp Leu Tyr
                85                  90                  95

Ala Asp Arg Ala Lys Arg Met Gly Asp Glu Pro Leu Tyr Thr Tyr Lys
            100                 105                 110

Ser Asp Asn Glu Trp Val Thr Val Thr Ala Asn Glu Phe Leu Ala Glu
        115                 120                 125

Val Arg Ala Val Ala Lys Gly Leu Leu His Tyr Gly Ile Lys Lys Gly
    130                 135                 140

Asp Gly Val Ala Phe Met Cys Arg Thr Ser Tyr Asp Trp Asp Leu Thr
145                 150                 155                 160

Asp Ala Ala Ile Met Ala Cys Gly Gly Val Leu Ala Thr Ile Tyr Asp
                165                 170                 175

Thr Asp Ser Ala Glu Gln Ile Arg Asn Ile Val Asn Asn Ser Asp Ala
            180                 185                 190

Arg Leu Leu Ile Val Gln Asp Ser Ala Met Arg Glu Lys Ala Glu Gly
        195                 200                 205

Ala Val Glu Glu Cys Pro Ser Leu Glu Arg Ile Leu Cys Ile Glu Thr
    210                 215                 220

Gly Ala Leu Asp Glu Ile Lys Ala Tyr Gly Ala Gly Ile Ser Asp Glu
```

```
            225                 230                 235                 240
        Glu Leu Asp Glu Arg Ile Asp Ser Val Lys Lys Thr Asp Leu Cys Ser
                            245                 250                 255
        Ile Val Tyr Thr Ser Gly Ser Thr Ala Ala Pro Lys Gly Val Glu Met
                            260                 265                 270
        Thr His Glu His Tyr Cys Gln Thr Ala Leu Asn Leu Pro Asp Tyr Met
                            275                 280                 285
        Pro Glu Leu Leu His Asn Lys Lys Asn Thr Ile Leu Leu Phe Leu Pro
                            290                 295                 300
        Gln Ala His Ser Phe Ala Arg Ala Ile Asn Tyr Ile Val Val Ala Ser
        305                 310                 315                 320
        Asn Met His Ile Tyr Ile Ala Ala Gly Ile Lys Thr Leu Ile Ser Asp
                            325                 330                 335
        Leu Gln Val Ala Lys Pro Ser Ile Met Ile Val Val Pro Arg Val Leu
                            340                 345                 350
        Glu Lys Val Tyr Asn Ala Ala Ser Gln Lys Ala Gly His Gly Pro Lys
                            355                 360                 365
        Gly Val Val Phe Ala Ser Ala Val Ala Ala Gln Asn Tyr Met Lys
                            370                 375                 380
        Glu Ile Ser Ala Asn Gly Lys Ala Ser Ala Leu Thr Arg Ala Arg Arg
        385                 390                 395                 400
        Ala Ala Phe Asp Pro Ile Val Tyr Ser Ser Leu Arg Glu Val Leu Gly
                            405                 410                 415
        Gly Arg Met Lys Trp Ile Val Ala Gly Gly Ala Pro Leu Asp Pro Glu
                            420                 425                 430
        Leu Leu Ala Phe Phe Arg Gly Ala Ser Val Pro Val Tyr Glu Gly Tyr
                            435                 440                 445
        Gly Leu Thr Glu Thr Thr Ala Pro Cys Ala Phe Asn Pro Leu Gly Thr
                            450                 455                 460
        Pro Phe His Ala Gly Ser Val Gly Val Ala Phe Pro Gly Phe Ser Leu
        465                 470                 475                 480
        Arg Ile Ala Glu Asp Gly Glu Ile Gln Val Lys Gly Arg Ala Val Phe
                            485                 490                 495
        Pro Arg Tyr His Lys Asn Asp Glu Ala Thr Glu Leu Ser Phe Thr Glu
                            500                 505                 510
        Asp Gly Trp Tyr Ala Thr Gly Asp Leu Gly Arg Ile Asp Asn Asp Gly
                            515                 520                 525
        Phe Leu Tyr Ile Thr Gly Arg Lys Lys Asp Leu Ile Ile Thr Ala Gly
                            530                 535                 540
        Gly Lys Asn Val Ala Pro Gly Pro Ile Glu Glu Ala Ile Gln Arg Cys
        545                 550                 555                 560
        Glu Phe Val Ser Gln Ala Leu Val Leu Gly Asp Lys Arg Pro Phe Ile
                            565                 570                 575
        Ser Ala Leu Ile Thr Leu Asp Glu Glu Ser Leu Arg Pro Trp Leu Ala
                            580                 585                 590
        Ala Lys Gly Leu Asp Glu Asn Met Ser Leu Glu Asp Ala Ser Gln Asn
                            595                 600                 605
        Ala Ala Val Arg Ala Glu Val Gln Lys Trp Ile Asp Gln Ala Asn Glu
                            610                 615                 620
        Gly Val Ser Arg Ala Glu Ser Val Arg Lys Phe Ile Ile Leu Pro Glu
        625                 630                 635                 640
        Glu Phe Thr Gln Glu Asn Gly Leu Met Thr Ala Ser Met Lys Val Ile
                            645                 650                 655
```

```
Arg Pro Lys Val Ile Lys Arg Tyr Ser Thr Leu Leu Asn Thr Gln Met
            660                 665                 670
Tyr Thr Lys Lys Lys
        675
```